United States Patent [19]

Smallbone et al.

[11] 4,134,012
[45] Jan. 9, 1979

[54] X-RAY ANALYTICAL SYSTEM

[75] Inventors: Allan H. Smallbone; Yury M. Gurvich, both of La Crescenta, Calif.

[73] Assignee: Bausch & Lomb, Inc., Rochester, N.Y.

[21] Appl. No.: 842,522

[22] Filed: Oct. 17, 1977

[51] Int. Cl.² ............................................. G01N 23/22
[52] U.S. Cl. ..................................... 250/272; 250/273
[58] Field of Search ........... 250/272, 273, 274, 277 R, 250/278, 279

[56] References Cited

U.S. PATENT DOCUMENTS 3,404,275  10/1968  Martinelli ............................. 250/272
3,710,104  1/1973   Pavlek .................................. 250/272

Primary Examiner—Craig E. Church
Attorney, Agent, or Firm—Theodore H. Lassagne

[57] ABSTRACT

An X-ray spectrometer is provided with two channels for detecting characteristic lines of the X-ray source after being scattered by a sample undergoing analysis, in addition to means for detecting electric signals primarily representative of the concentrations of analytes in the sample. In this way, data is collected which facilitates corrections of the measurements corresponding to individual analytes for deviations from linearity of intensity caused by variations in interelement effects, and by variations in total-solids concentration, or density, of the slurry, or matrix, in which the analytes are distributed, and by variations in particle size of the total-solids in the sample. Correction of measurements of total-solids concentration and average particle size of the matrix for each other and for effects of analytes, may also be made.

The invention may be applied to slurries where the total-solids concentration and particle size may both vary simultaneously from sample to sample, and to dried, solid, or powdered samples where density and particle size may both vary in a similar way.

In an automatic control system, the sample is taken from a slurry and the output signal is employed to control the process to match a norm. The invention may be employed to improve recovery of desired materials and to reduce the discharge of waste materials likely to cause pollution.

22 Claims, 8 Drawing Figures

X-RAY ANALYTICAL SYSTEM

BACKGROUND OF THE INVENTION

1. Field of the Invention

The present invention relates to spectroscopy, and more particularly to improvements having as a purpose the enhancing of the capabilities and the accuracy of spectroscopic analyses utilizing scattered X-rays and fluorescence that has been excited by X-rays.

2. Description of the Prior Art

The chemical composition and/or physical characteristics of materials input to industrial processes, material occurring at intermediate stages of such processes, and especially the tailings discharged, require monitoring for the purposes of process control. To be of maximum utility, the results of such monitoring need to be made available as closely as possible in time to the passage of the material through the process. Because chemical laboratory analysis of samples involves excessive delay in the availability of its results, X-ray spectroscopic analysis of such materials essentially simultaneously with their occurring in processing has been widely adopted.

Spectroscopic analysis of X-ray induced fluorescence thereof has, for example, permitted on-stream analysis, essentially in real time, of flowing slurries of metal-bearing mixtures in the course of ore processing. However, the accuracy of the results obtainable in such analyses has been adversely affected by variations in particle size of the solids, in concentration of solids in a slurry, as well as by interelement effects, and a number of efforts have been made to eliminate or minimize inaccuracies so arising.

Anderman and Kemp, in U.S. Pat. No. 2,897,367, described in 1956 a system employing means for detecting an X-ray beam at a wavelength characteristic of the analyte, or component, the concentration of which was being sought, and also detecting another X-ray beam emerging from a sample at a wavelength different from any characteristic of any component of the sample, and compensating for variations in physical characteristics, including particle size, of the sample by measuring the ratio of the intensity of the first beam to the intensity of the second beam.

Furbee and Bernstein, un U.S. Pat. No. 3,150,261, described in 1962 a system employing background radiation in compensating for variations in the solids-to-liquids ratio in a slurry.

Lucas-Tooth and Pyne in "Advances in X-Ray Analysis", 1964, 7, pages 523 et seq., described the application of computer techniques based on chemically analyzed samples of steel for correcting for interelement effects in spectroscopic X-ray analyses.

Carr-Brion and Bramwell in U.S. Pat. No. 3,749,910 described in 1970 a system using background radiation in determining the size of solid particles in a slurry.

U.S.S.R. Inventor's Certificate No. 448,374, issued to Yuri M. Gurvich et al, October 30, 1974, described a novel method for analyzing slurries by means of X-ray spectroscopy methods, which involved making measurements of intensities of certain radiation other than the characteristic lines of the elements of interest to determine the concentrations of such elements independently of particle size. In the method described by Gurvich et al, use is made of an X-ray spectrometer, which was called a quantometer, but which is quite different from the ARL quantometer referred to hereinafter. In the method described there, measurements were made of the intensity of two lines of fluorescent radiation from the material constituting the back side of the flow cell after the radiation had traveled back through the slurry. Gurvich et al also recognized the possibility of using one or two areas of radiation scattered by the slurry at different wavelengths, including one characteristic line of the anode of an X-ray tube that supplied the exciting radiation.

The method described by Gurvich et al was intended to take advantage of the influence of total-solids concentration and particle size, on the intensity of both selected fluorescent lines of the back side of the flow cell or two areas of scattered radiation, one of which may be a source line. However, this method is far from fully effective for several reasons.

First, fluorescent lines from the back side of the flow cell can be used practically only for slurries with low absorption properties, namely, poor ores and tails of industrial processes. For rich ores or concentrates, such lines are highly attenuated by their passage through the sample in the cell and, in fact, absorbed almost completely in the first 1 to 2 mm of the cross section of the slurry's stream. Besides, the intensities of lines from the back side of the cell depends highly on geometrical conditions of measurement, including even slight variation of distance between the source of the primary X-ray beam and the flexible wall of the flow cell composed of say, capton or mylar. The intensities of such lines also depend highly on any sedimentation of solids that accumulate on the back wall of the cell. Thus, such measurements are unreliable.

Secondly, Gurvich et al disclosed for on-stream slurry analysis as a source of primary radiation, X-ray tubes with a target which supplied only one characteristic line that was scattered by the sample and detected.

Furthermore, the two wavelengths that Gurvich et al suggested be used, are both hard and are such that if they could both be detected they would fail to show any substantial difference in variation of intensity as a function of solids concentration and particle size in the slurry.

Even with the techniques disclosed in the prior art, however, it still was not possible to obtain on-stream analyses of slurries by X-ray spectroscopy comparable in accuracy to analyses obtainable by chemical analysis, especially with respect to the lighter elements. The on-stream analysis of this invention provides a much more rapid means of obtaining accurate assays of a flowing product since with it, samples can be assayed intermittently for up to 11 elements, for example, every 30 seconds with each of a large number of streams, perhaps 20 or 30, being assayed every 5 to 15 minutes in "real time".

In addition to the need for higher accuracies of assays, smelters are being penalized for excessive discharge of calcium, sulphur, or, in some cases, silicon in order to encourage the operators to reduce pollution and prolong the life of their furnaces; thus increasing the desirability of making possible on-line measurement of the lighter elements, calcium, sulphur, and silicon. Accurate measurement of sulphur concentration is also needed for general purposes and especially where copper ores are being processed.

It is a primary object of the present invention therefore, to provide a system in which, by accurately measuring these various elements on-line and compensating for physical characteristics and interelement effects, a complete assay may be obtained of the entire sample providing improved accuracy with respect to all components of interest, both components to be recovered and components to be suppressed.

SUMMARY OF THE INVENTION

In the best mode of practicing the present invention, characteristic radiation of the material forming the anode is scattered by the slurry, and is detected in two different areas of the spectrum, and the intensity of that detected radiation is measured. These measurements are combined with the other X-ray spectroscopic measurements made on the sample to provide for simultaneous determination of the concentration of the various analytes of interest in the slurry and also the total-solid concentration and average particle size. The various measurements may also be combined to produce measures of the composition of a sample and the density and particle size of the material tested if it is in the form of a solid, such as a briquette or powder. The characteristic anode lines used for this purpose are of widely different wavelengths, one being soft and the other being hard, but both being within the range of wavelengths that are detectable and measurable in a wide-range quantometer. By utilizing the characteristic lines of widely different wavelengths from the X-ray source, the accuracy of the determination of total-solid concentration or density and particle size and the concentration of various components of a slurry or other sample, is increased because the intensities of the two scattered characteristic source lines vary with concentration and with particle size in widely different amounts.

The mathematical techniques employed for calculating the concentrations of individual elements, the concentration of total-solids, and the density of solids, and particle size are rather complex. They are described in sufficient detail below to enable one skilled in the art to utilize the invention effectively. Briefly though, each quantity to be determined, such as concentration or particle size, is expressed as a high degree multiple regression or polynominal equation including a constant term, a linear term proportional to the intensity of radiation of one or several elements of interest where there are such principal elements, a series of quadratic or cross-product terms in which the intensity due to an element as multiplied by itself and by the respective intensities of other detected beams, and quadratic terms in which the intensity of each of the scattered beams having their origin in the X-ray anode is multiplied by the intensities of other beams. In addition, there may be third degree terms. By applying such equations to the measurements, the concentration of solids, some characteristic of particle size, and the concentration of each elementary component thereof of interest, may be accurately determined.

In the best mode of practicing the invention, incoherent scattered radiation is detected and measured as distinguished from coherent scattered radiation. These two types of radiation are distinguished by the fact that the coherent scattered radiation has the same wavelength as the incident radiation and the incoherent scattered radiation has a slightly different wavelength. The difference in wavelength of coherent and incoherent scattered radiation is 0.024Å. The occurrence of incoherent scattered radiation is attributed to Compton-type collisions. The reason for selectively detecting coherent radiation in preference to coherent radiation lies in the fact that their intensities vary entirely differently as functions of total-solid concentration and particle size. More particularly, it has been found that the variation of intensity of the scattered radiation as a function of solid-state concentration and particle size is much more for incoherent radiation than for coherent radiation.

The present invention is distinguished from the prior art laregly by the fact that two or more characteristic lines of a source of radiation are scattered from the sample and those scattered lines are detected and measured along with lines that are characteristic of the elements of interest in the mixture undergoing analysis; by the further fact that it is incoherent scattered source radiation that is detected and measured in preference to coherent scattered source radiation; by the fact that at least one of the scattered source lines is soft and at least one of the other scattered source lines is hard; and by the fact that the proportion of scattered radiation for the two source lines detected varies with wavelength as a function of total-solid concentration to a greatly different amount than it varies with particle size.

By exciting a sample with lines characteristic of the source that have wavelengths entirely different from the characteristic lines of the sample, measuring the intensities of the source lines as well as the sample-component lines, data is collected that leads to a more accurate determination of the composition of the sample by X-ray spectroscopy than heretofore. The invention lies both in the method and apparatus for accomplishing these superior results.

This invention makes possible a more rapid analysis and control of processes without greatly increasing the cost thereof. The slight increase in cost providing an improved system for achieving the analysis and control in question, is far less than the savings that can result therefrom.

BRIEF DESCRIPTION OF THE DRAWINGS

The invention is described hereinafter with reference to the accompanying drawings and a number of examples.

IN THE DRAWINGS

Figure 1:
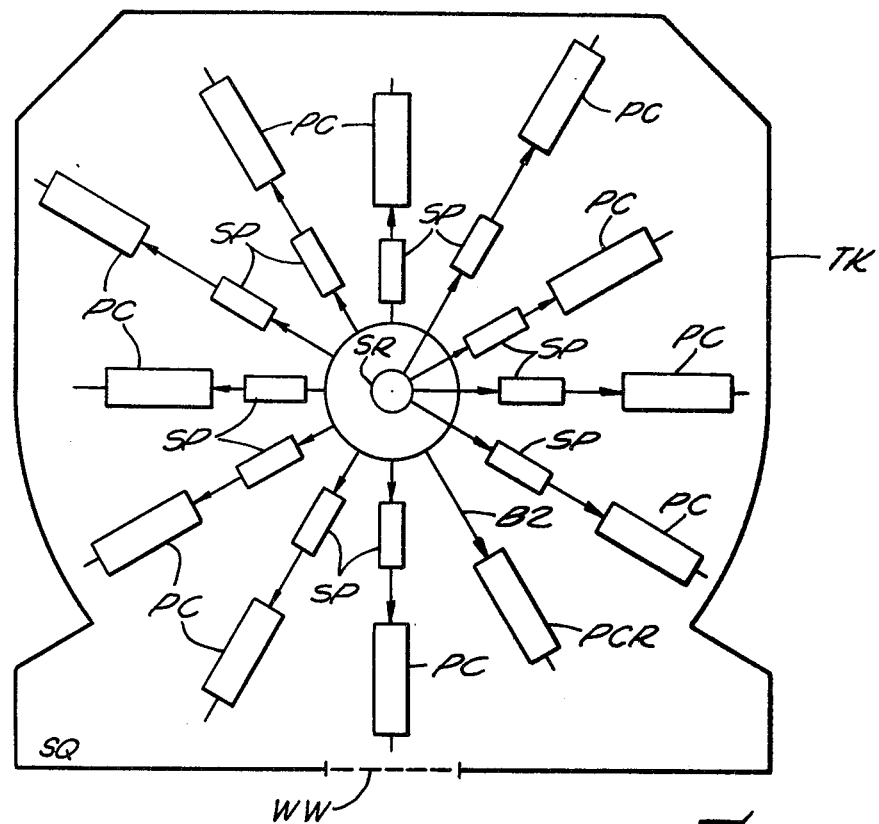
Figure 2:
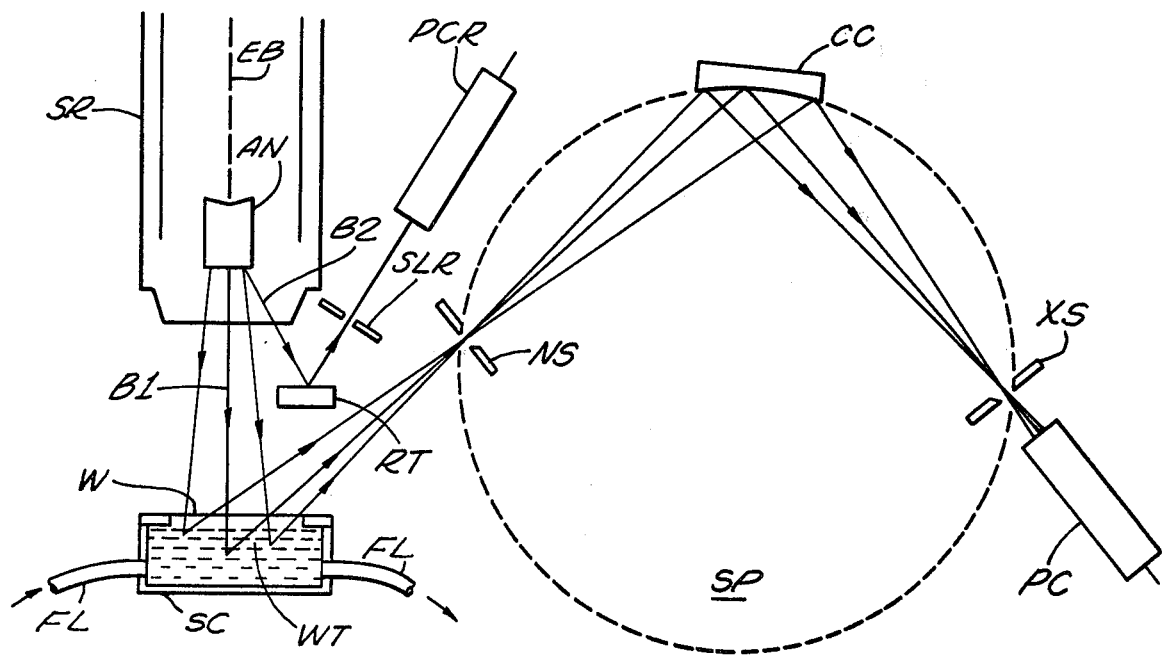
Figure 3:
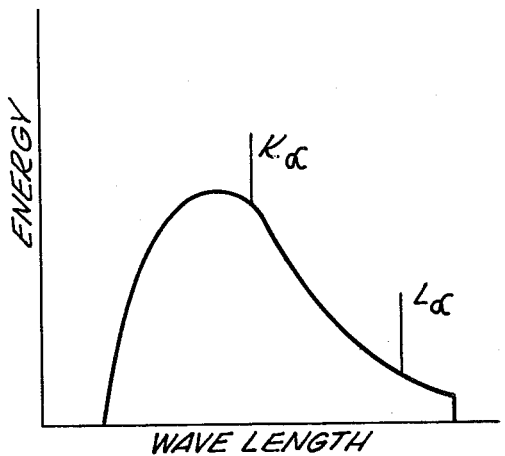
Figure 4:
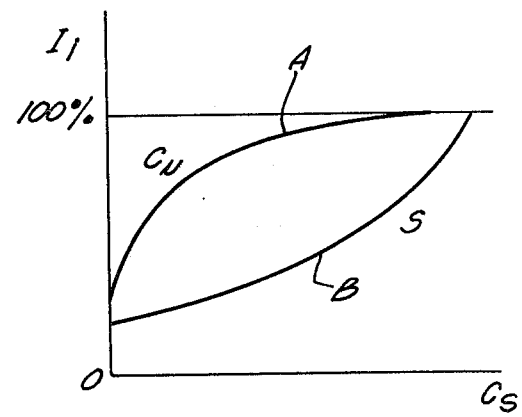
Figure 5:
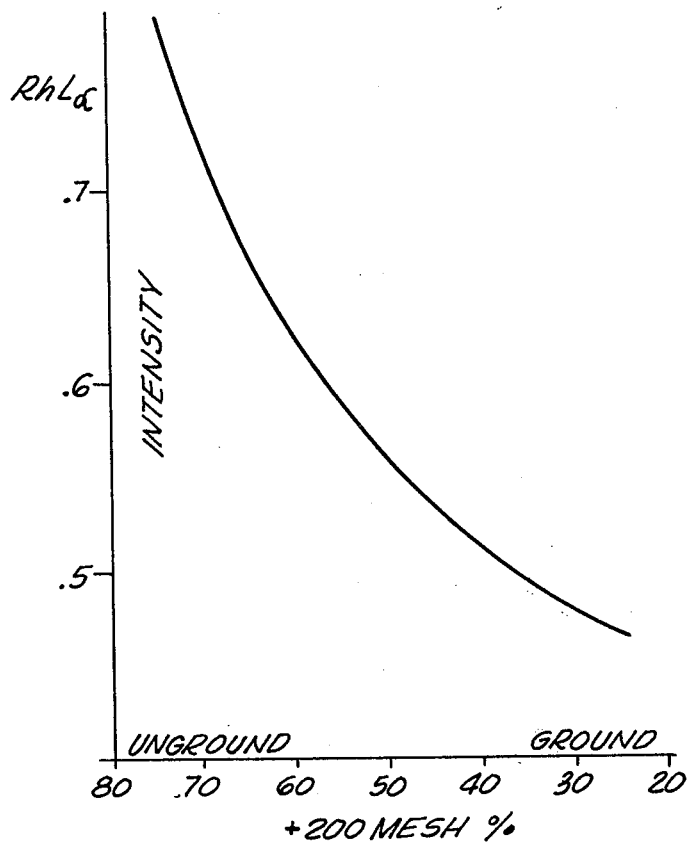
Figure 6:
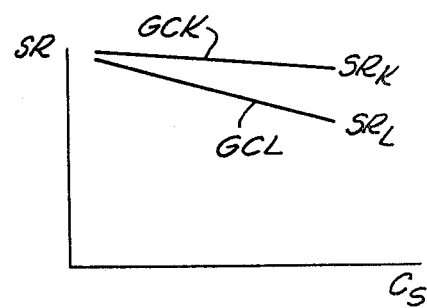
Figure 7:
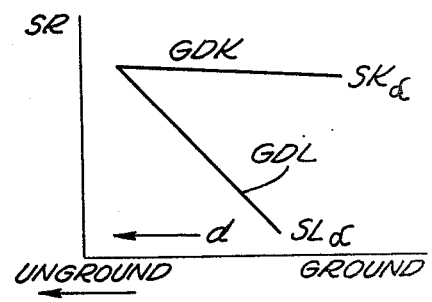
Figure 8:
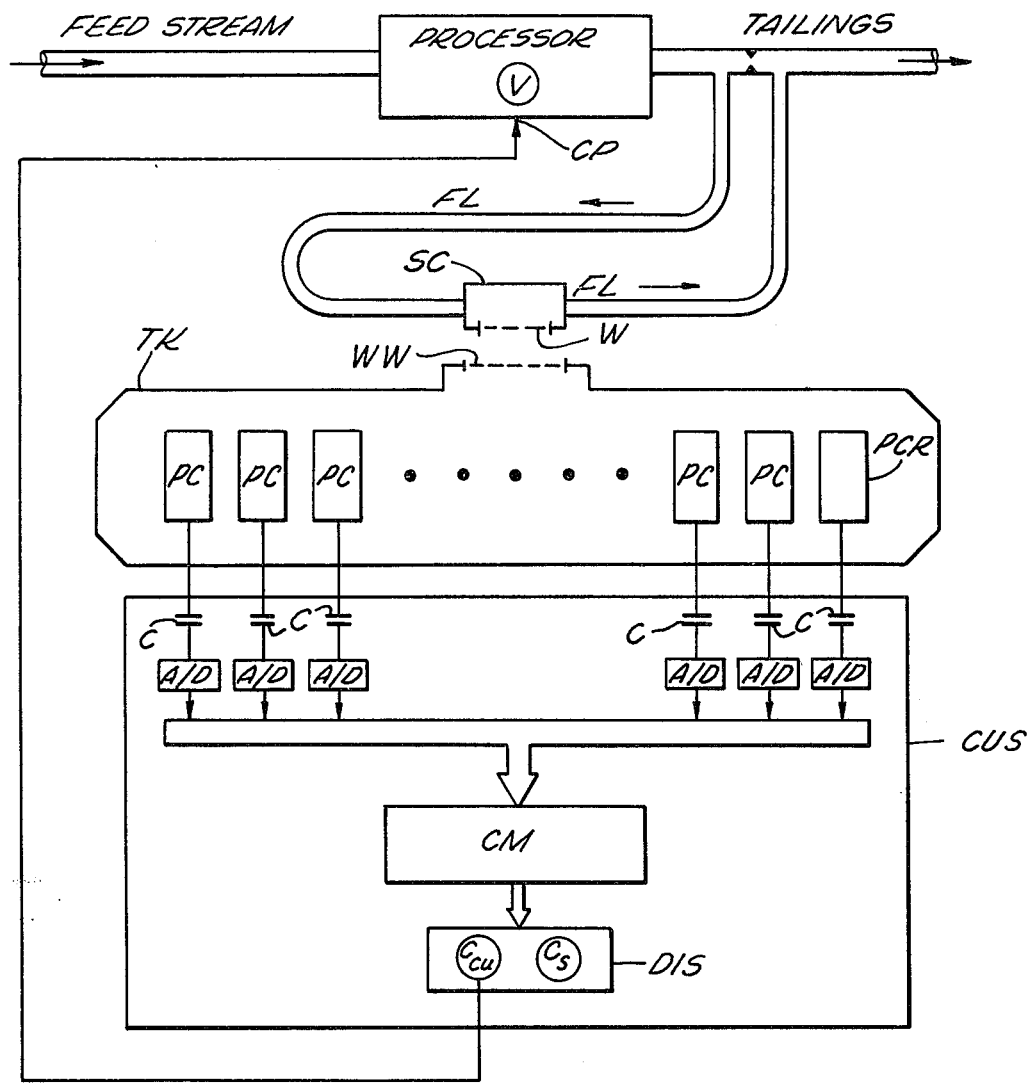

FIG. 1 is a schematic diagram of a quantometer modified in accordance with the present invention;

FIG. 2 is a drawing employed for explaining certain aspects of the invention;

FIG. 3 is a graph representing the spectrum of the X-rays emitted from a rhodium anode of an X-ray tube;

FIG. 4 is a graph showing how the intensity of the fluorescent radiation emerging from various components of a sample varies as a function of the concentration of the total-solids in the sample independently of variations in particle size;

FIG. 5 is a graph representing how the intensity of scattered radiation varies as a function of particle size at a given wavelength independently of variations in concentration of total-solids in a slurry;

FIG. 6 is a graph representing the manner in which the K$\alpha$ and L$\alpha$ characteristic lines of rhodium vary in intensity in the scattered radiation of slurries of different total-solid concentration $C_s$ if the particle size is constant;

FIG. 7 is a graph representing the manner in which the K$\alpha$ and L$\alpha$ characteristic lines of rhodium vary in intensity as a function of particle size if the total-solid concentration is constant; and FIG. 8 is a schematic diagram of a system for automatically generating the output signals and for controlling a unit in which materials are processed.

DESCRIPTION OF THE PREFERRED EMBODIMENT

In many processing systems, several processing units are arranged in cascade with the output of one being used as input to another. In many such cases, the later units need to be adjusted or controlled in accordance with the composition of the slurry fed to it, to attain maximum recovery of a particular material or minimum yield of another. And in some cases, a processing unit needs to be regulated in accordance with the composition of its output for similar reasons. Such regulation or control can be aided by X-ray spectroscopy. According to this invention, the composition may be measured more precisely than heretofore and as a result, the efficiency or effectiveness or reliability of processing units may be improved.

The ARL quantometer, a multiple-channel X-ray spectrometer, manufactured by Applied Research Laboratories, Inc., of Sunland Cal., is commonly employed for process control. In this system, the sample undergoing analysis is excited by primary X-rays emitted from a metal anode of an X-ray tube and a number of detectors, or proportional counters, are included in such an instrument, along with corresponding monochromatizing diffraction crystals so that each proportional counter will detect a narrow band of secondary characteristic fluorescent radiation from each of the respective principal components of the sample. In such an instrument, the outputs of the proportional counters are fed through coaxial conductors to integrating capacitors across which voltages are developed that represent the intensities of respective fluorescent beams. These voltages are measured to indicate the intensities of the respective lines (but not necessarily to the same scale). The spectrometer mentioned also employs an auxiliary "target" that is exposed to the exciting X-ray beam and provides a reference standard. The intensity of the fluorescent radiation excited in the target is measured in a similar way, but without selection of a narrow range of wavelengths, to ascertain the intensity of the primary X-ray beam that excites the sample. This measurement is employed to correct the measurements of the characteristic lines for fluctuations of intensity of the exciting X-ray beam. In this way, precise measurements are obtained that are substantially independent of the intensity of the exciting beam.

Such prior art measurements, however, are dependent to some extent on the concentration of the solids in the slurry, and also upon the sizes of the particles in the slurry. Consequently, the signals produced by the proportional counters, even after correction has been made for fluctuations in intensity of the exciting X-ray beam, are subject to error because of changes that occur in the concentration of the solids in the slurry and because of changes that occur in the size of the particles as a result of the processing operations.

This invention provides a new arrangement for producing measurements of the concentrations of individual components of the solid part of a slurry that are independent of variations in the total amount of solids in a slurry and particle size.

Further difficulty in the analysis of slurries, as well as other compositions, by means of X-ray spectroscopy, involves what is known as the interelement effect. In this connection, it is well established that the intensity of the secondary fluorescent radiation corresponding to a characteristic line of any element, depends not only upon the amount of that element present in a mixture, but also on the amounts of other elements that are present. For example, secondary fluorescent radiation generated by one element in a slurry in response to an exciting beam may be absorbed by other elements that are present and hence its intensity depends upon the concentrations of those other elements. Likewise, fluorescent radiation characteristic of an element may be excited not only by the primary X-ray beam supplied by the X-ray tube, but also by secondary fluorescent radiation that is excited in other elements by the primary X-ray beam. In the first case, the characteristic fluorescent radiation may be attenuated by the presence of other elements. In the second case, it may be enhanced by the presence of other elements. Attenuation and enhancement of fluorescent radiation from an element may also occur in some other ways related to the presence of other elements.

This invention produces a measurement of any particular element that is substantially proportional to the concentration of that element independently of interelement effects as well as being independent of the total-solid concentration and particle size.

Referring to FIGS. 1 and 2, there is illustrated a multi-channel X-ray spectrometer that embodies the invention. The spectrometer SQ is a modified 44,500 model spectrometer manufactured by Applied Research Laboratories and known as a quantometer. The spectrometer of FIGS. 1 and 2 comprises a source SR of primary X-rays created by bombarding an anode AN by means of an electron beam accelerated in an electric field of say 50,000 volts. The anode or target AN is composed of rhodium.

The radiation emitted from the anode has both a continuous component and several characteristic-line components, as illustrated in FIG. 3. It is important to note that among the characteristic-lines of the spectrum there are two strong lines, namely, a hard X-ray line known as the rhodium $K\alpha$ line $RhK\alpha$ and a soft X-ray line known as the rhodium $L\alpha$ line $RhL\alpha$.

As indicated in FIG. 2, the exciting radiation emerges from the anode AN as a diverging beam having parts B1 and B2. The first beam B1 enters a sample region where it passes through a transparent window W into a flowing slurry under investigation. The second beam B2 of X-rays strikes a reference target RT composed of brass that provides an external standard.

The radiation scattered from the reference target RT passes through a slit SLR without dispersion to a proportional counter PCR. This counter produces an electric signal proportional to the intensity of the radiation including the first beam B1 emitted from the anode AN. The beam B2 is sometimes referred to as the non-dispersed beam. The electric signal that it produces in the proportional counter PCR is used to compensate for changes in intensity of the exciting beam. The two beams B1 and B2 are really parts of the same beam. They have the same spectrum and their intensities rise and fall together.

Signals generated by the proportional counter PCR may be employed for correcting other measurements for changes in intensity of the beam.

The first beam B1 is incident upon and partially penetrates the sample. The incident X-ray beam excites various components of the sample causing them to fluoresce, that is, to emit secondary radiation having wavelengths characteristic of the individual components. The fluorescent radiation includes both Kα lines and Lα lines, and sometimes other lines of the component elements. Scattered radiation having a spectrum like that of the radiation from the X-ray source is also emitted in various directions from the sample. In the multi-channel X-ray spectrometer of this invention, separate channels are employed to detect the intensity of the emerging radiation at a plurality of wavelengths, some of which correspond to fluorescent radiation from the various analytes, or components, of interest in the slurry and two of which correspond to the characteristic line radiation of the material composing the anode AN of the X-ray tube SR. Each of these channels includes a separate monochromatizing X-ray spectrometer SP of the Johanson type. Each of these spectrometers comprises a primary, or entrance, slit NS, a curved dispersing crystal CC, and a secondary, or exit, slit XS is arranged on a Rowland circle so as to select radiation of a predetermined wavelength for emergence from the exit slit and to impinge upon the detector, or proportional counter PC.

Table I lists the wavelengths for the Kα and Lα lines for various elements to which reference is made herein.

TABLE I

| Element | Atomic No. | Kα(A) | Lα(A) |
|---------|------------|-------|-------|
| Si | 14 | 7.13 | |
| S | 16 | 5.37 | |
| Ca | 20 | 3.36 | |
| Fe | 26 | 1.94 | |
| Ni | 28 | 1.66 | |
| Cu | 29 | 1.54 | |
| Mo | 42 | 0.71 | |
| Rh | 45 | 0.61 | 4.60 |
| Pb | 82 | | 1.18 |

The proportional counters PC are designed to produce maximum response to X-ray radiation over predetermined bands. By way of example, proportional counters listed in Table II have maximum response in the wavelength ranges indicated.

TABLE II

| Proportional Counters | Wavelength Range (A) |
|-----------------------|----------------------|
| Krypton Multitron | 0.36 – 1.5 |
| Argon Multitron | 1.5 – 2.5 |
| Neon Multitron | 2.5 – 3.8 |
| Be window Geiger Exatron | 3.8 = 10.00 |
| Al window Geiger Exatron | above 8.00 |

When X-ray radiation in low wavelength ranges is being detected and measured, the tank TK is filled with helium.

In the ARL quantometer employed in this invention, the full range of all the channels extends from about 0.35Å to about 10.00Å. X-rays that have wavelengths in the range between about 0.2Å and about 0.8Å are called hard, and X-rays that have wavelengths between about 2.5Å and about 10.0Å are called soft. The two rhodium lines lie far on opposite sides of the geometrical means of the range of the quantometer employed, the Kα line being hard and the Lα line being soft. Sometimes the wavelengths themselves are referred to as hard or soft as the case may be.

In practice, a plurality of sample cells SC are employed in flow lines FL-FL that carry slurry from various parts of an ore processing plant. These sample cells are mounted on a rack which is automatically moved intermittently to present one sample cell SC at a time for exposure to exciting X-rays at the window WW of the tank TK.

The proportional counters PC include ionization chambers for detecting the X-rays. attenuators associated with the ionization chambers bring all the intensity signals within an easily measurable range. In the particular quantometer to which the invention has been applied, the "attenuators" are in the form of arrays of series-connected resistors with selectable taps that are used for setting the accelerating voltages of the ionization chambers.

The proportional counters produce electric charges at their outputs in proportion to the energy of the X-ray photons striking their corresponding detecting elements. These charges are accumulated on corresponding capacitors. At the beginning of a measurement, the capacitors are discharged. As the charges accumulate on the respective capacitors, they produce voltages proportional to the total intensity detected at the corresponding wavelengths. The constant of proportionality is not the same for all channels, but depends on the characteristics of the components, the nature of the ionization chambers, and the settings of the attenuators in the individual channels.

The proportional counters may also be used with scaling circuitry. In this case, the attenuators are adjusted for that photon-produced charges at the outputs of the proportional counters are of an appropriate magnitude for the signal conditioning circuitry of the scalers. At the beginning of a measurement, the scalers are reset to 0. As the counts accumulate on the respective scalers, they produce cumulative counts representative of their total intensities detected at their corresponding wavelengths.

In FIG. 4, there are represented two typical graphs showing how the intensities of characteristic lines due to different components of a slurry, namely, sulphur and copper, vary as a function of the total-solid concentration. Abscissae represent concentration of solids and ordinates represent the intensities of the characteristic lines. Note that graph A is concave downwardly and graph B is concave upwardly. A straight-line graph (not shown) would occur if the atomic number Z were about equal to the effective atomic number $Z_{ef}$ of the gangue, or matrix. In this connection, experience has shown that the effective atomic number of the gangue is in the neighborhood of 20. Departures from linearity in the graphs also depends upon interelement effect.

TABLE III

| Analytical Line | λ(A) | $I_{gr.}/I_{ungr.}$ |
|-----------------|------|---------------------|
| Si $K_\alpha$ | 7.1 | 2.04 |
| S $K_\alpha$ | 5.4 | 1.30 |
| Ca $K_\alpha$ | 3.4 | 1.29 |
| Cu $K_\alpha$ | 1.5 | 1.14 |
| Zn $K_\alpha$ | 1.4 | 1.07 |
| Pb $L_\alpha$ | 1.2 | 1.05 |

In Table III, there are represented data that show the influence of particle size on intensity of fluorescent radiation of some main elements of slurries. Here it is shown that the intensity of each line changes when particle size varies and that the amount of this change depends on the wavelength of the line. Both the data of FIG. 4 and Table III demonstrate that it is important to make correction for variation in total-solids concentration and for variations in particle size. In the specific embodiment of the invention described herein, this is done by basing such corrections on the intensity of incoherent scattered Kα and Lα lines of rhodium.

In addition, in accordance with this invention, two similar channels are provided that have spectrometers and proportional counters designed to facilitate measurement of the intensity of the two characteristic rhodium lines that are scattered by the sample.

It has been found that the concentration of any particular element in a slurry can be calculated from an equation of the following general type:

$$C = a_o + \sum_{j=1}^{n} a_j I_j + I_i \sum_{j=1}^{n} b_j I_j + I_{SK} \sum_{j=1}^{n-1} d_j I_j + I_{SL} \sum_{j=1}^{n-2} e_j I_j \quad (1)$$

where
  C = concentration of the element in question
  $I_j$ = intensity of the characteristic line j of the elements in the slurry and the element of which the anode of the X-ray tube is composed; thus, $I_j$ sometimes refers to $I_{SK}$ and $I_{SL}$ where K refers to the Kα line and L refers to the Lα line of the material of the anode AN, and
  $a_o, a_j, b_j, d_j, e_j$ are experimentally determined parameters. These parameters may be positive or negative as the case may be so as to correct for concave upwardly and concave downwardly characteristics of the graphs that represent the interelement effects.

It is found experimentally, that many of the parameters may be set at 0 and that the total number of terms in the equations for the concentrations of many components, is often less than the number of elements of interest in the slurry.

A similar equation may be written for calculating the concentration $C_s$ of the total-solids in a slurry, or the particle size (average diameter d) of the total-solids. But in these cases, the third term of equation (1) is not present. Thus, the equation for the concentration of the total-solids or the particle size may be written as $$C_s (\text{or } d) = a_o + \sum_{j=1}^{n} a_j I_j + I_{SK} \sum_{j=1}^{n} d_j I_j + I_{SL} \sum_{j=1}^{n-1} e_j I_j \quad (2)$$

It is to be understood, of course, that the values of the parameters $a_o$, etc., usually differ from one component to another, there being a different set of parameters for each element and also for the concentration of total-solids $C_s$ and also for the particle size d. The values of the parameters also depend upon from what part of the processor the samples are taken.

In FIG. 5, there is illustrated how the intensity of the rhodium Lα line RhLα scattered by the slurry varies as a function of particle size. While the curve represents a good fit for actual data, a straight line fit might also very well be satisfactory, especially when the variation of average particle size is not very great.

In FIG. 6, there is illustrated how the intensities of the two rhodium lines scattered by the slurry vary as a function of the concentration of total-solids in the slurry. And FIG. 7 indicates how the intensities of these two lines vary with particle size. In these figures, straight-line relations are assumed to represent the phenomena. Note that these two graphs of FIG. 6 diverge only slightly, while those of FIG. 7 diverge greatly. Relations similar to those represented by FIG. 6 and FIG. 7 apply to variations of density and average size of particles of solid samples of ore in solid samples.

The graph GCK represents the manner in which the intensity of the scattered radiation varies with total-solid concentration of a slurry for the Kα line of rhodium. The graph GCL represents the manner in which the intensity of the scattered radiation varies with total-solid concentration for the Lα line of rhodium. The graph GDK represents the manner in which the intensity of the scattered radiation varies with the total-solid particle size for the Kα line of rhodium, and the graph GDL represents the manner in which the intensity of the scattered radiation varies with particle size for the Lα line of rhodium. For best effects, the absolute value of the discriminant of these four variations is large. The discriminant may be written as $$D = \begin{vmatrix} \dfrac{C_s}{I_{K\alpha}} \dfrac{dI_{K\alpha}}{dC_s} & \dfrac{d}{I_{K\alpha}} \dfrac{dI_{K\alpha}}{dd} \\ \dfrac{C_s}{I_{L\alpha}} \dfrac{dI_{L\alpha}}{dC_s} & \dfrac{d}{I_{L\alpha}} \dfrac{dI_{L\alpha}}{dd} \end{vmatrix}, \text{ or }$$

$$\dfrac{C_s d}{I_{K\alpha} I_{L\alpha}} \begin{vmatrix} \dfrac{dI_{K\alpha}}{dC_s} & \dfrac{dI_{K\alpha}}{dd} \\ \dfrac{dI_{L\alpha}}{dC_s} & \dfrac{dI_{L\alpha}}{dd} \end{vmatrix}$$

In this equation, the derivatives represent the average slopes over the ranges of interest. In a more complete expression for the discriminant, interelement effects and influence of other fluorescent lines would be taken into account.

Comparing the two FIGS. 6 and 7, it is to be noted that there is a much greater variation in intensity of the two lines for a given proportional change of particle size than there is for the same proportional change in total-solid concentration. The wide disparity in the ratio of the slopes in the two cases helps achieve accurate analyses in which corrections are made through the medium of equations (1) and (2) by taking into account the intensities of the scattered rhodium lines. This contrast in relative slopes for total-solid concentration and for particle size is found to be greater if incoherent scattered radiation is detected and measured than if coherent scattered radiation is detected and measured. In other words, the absolute value of the discriminant is greater for the incoherent scattered radiation than it is for the coherent scattered radiation. Stated differently, the variation of the scattering coefficients of the sample at the two source-line wavelengths as a function of the concentration of total-solids in the sample, are substantially different from the variation of the scattering coefficients at said two wavelengths as a function of particle size of the sample.

In this connection, it is to be borne in mind that the wavelengths of the Kα and Lα characteristic lines of rhodium are those set forth in Table I and that, due to the Compton-effect, each of these additional lines has a wavelength that is 0.024A different from the Kα and Lα lines. It is well known that the line of unchanged wavelength is coherent, whereas the Compton-effect lines of different wavelength are incoherent.

Advantage is taken of these experimentally determined facts by designing the spectrometers that detect the scattered rhodium radiation to selectively detect the incoherent radiation corresponding to the Kα and Lα lines and at the same time to suppress the neighboring coherent radiation. This selective detection of incoherent radiation is accomplished in well known ways by using spectrometers of high resolving power.

The X-ray source may be in other forms than an X-ray tube. For example, the X-ray source may be in the form of a blend of radioactive material of long half-life that produces X-rays of two wavelengths suitable for use in the analysis. Such a material may be in the form of a blend of tritium and natural zirconium ($H^3/Zr$) or tritium and natural aluminum ($H^3/Al$). The first mentioned material emits soft X-rays having a wavelength of 6.09Å and a continuous spectrum of hard X-rays having a peak wavelength slightly above 0.69Å. The second blend yields soft X-rays having a wavelength of 7.95Å and also such a continuous spectrum of hard X-rays. The hard X-rays are generated by $\beta$ rays that are emitted by tritium and which bombard the other material to cause it to fluoresce to emit the soft X-rays mentioned. The hard X-rays have their origin in the bremstalling, or breaking, effect. Two advantages flow from the use of such a source of X-ray radiation. One advantage lies in the fact that there is no need for use of a power supply, thus making the instrument more portable and less expensive. Another advantage that flows from using such a source of X-ray radiation involves the fact that the intensity of the radiation does not vary significantly as a function of time and hence no corrections need be made for variations in intensity of the source, as previously mentioned.

The intensity measurements I represented in equations (1) and (2) are not absolute measurements, but are merely magnitudes of electric voltage (or pulse count) produced at the output of the respective proportional counters. As mentioned before, the proportional counters have different characteristics so that their outputs are not to the same scale. Furthermore, the circuitry associated with the proportional counters includes attenuators that are manually manipulated experimentally to bring the readings of the various counters within a manageable range. Accordingly, where values of the various parameters $a_0$, $a_1$, etc., are indicated below, no particular significance is to be attached to the relative values of parameters in any single equation, but comparison of values in different equations that represent different concentrations or particle size or components in accordance with the equation (1) and equation (2), are significant and gives some clue to the sensitivity of the method to the various measurements.

General Procedure

In accordance with the present invention, an arrangement is provided in which X-rays from a radiation source are directed to a sample, such as a portion of a slurry, and the intensity of scattered radiation and fluorescent radiation from the sample, is measured at a number of wavelengths at least 2 greater than the number of analytes in the sample. In addition, as mentioned above, non-dispersed radiation from a reference target, or external standard, is detected, and its intensity measured. Stated simply, the intensity of radiation of a number of wavelengths characteristic of the components in the sample is detected and, in addition, the intensity of radiation at two wavelengths characteristic of the source and radiation scattered by the sample is also detected, to correct the other measurements for variations in the intensity of radiation of the source.

The problem confronting the analyst is to develop a formula like that represented by equations (1) and (2) for each main component of interest for the general type of sample under investigation, and then to apply that formula to measurements made on samples of unknown composition. By way of example, the samples may be from sequentially developed parts of a slurry of a continuous operation. To achieve this result, a large number of samples compared to the maximum number of terms needed in the equations, are separated from the slurry under investigation. These samples are then analyzed chemically as well as by the X-ray system described above. In this way, an overdetermined set of equations is obtained and these equations are then analyzed by conventional methods to determine the best-fit set of parameters $a_0$, $a_1$, $a_2$, $b_1$, $b_2$, $b_3$, etc. By way of example, if two equations for concentration are to be developed having eight parameters each, the number of samples should be larger than 18. The number of terms needed in the equation for determining the concentration of any particular analyte, depends to some extent on the other components present and the range of concentration likely to be encountered in the slurry.

Each of the equations of the overdetermined set is of the kind represented by the foregoing equations with the chemically determined concentrations substituted for the C values, and the measured intensities I of the various characteristic lines. In effect, values of the parameters are the "unknowns" that are to be found in the calibration step, whereas both the intensities of the X-ray beams and the chemically determined concentrations $C_i$ of the various components i, are the "knowns".

Once having determined the values of the parameters for the slurry under investigation, later X-ray determinations of composition may be made of other similar slurries, and the concentrations of the components of interest calculated from the X-ray measurements.

A certain amount of experimentation is to be expected in selecting the number of terms and in selecting the number of reference samples to employ to determine the values of the parameters. But once having established the set of parameters for a slurry, the resultant equations may be employed to determine the composition of other samples of slurry to a much higher degree of accuracy than has heretofore been possible without the use of the measurements of the extra characteristic lines from the radiation source.

Example In this example, we refer to the results obtained from calibration of a slurry occurring in the bulk circuit of a system for processing ore bodies that included the elements calcium (Ca), silicon (Si), iron (Fe), copper (Cu), molybdenum (Mo), sulphur (S), and lead (Pb).

In this case, 72 reference samples were employed for determining the equations for the concentration of copper and sulphur. These two equations read as follows:

$$C_{Cu} = 0.0513 + 0.0398*I_{Cu} - 0.001046*I_{Si}*I_{Cu} + 0.002659*I_{Ca} - 0.00916*I_{RhL\alpha}*I_{Fe} + 0.0575*I_{Mo}*I_{RhL\alpha} - 0.01914*I_{RhK\alpha} \quad (4)$$

$$C_S = -0.275 + 1.306*I_S + 0.108*I_{RhL\alpha}*I_{Pb} + 0.022*I_{RhL\alpha}*I_{Cu} - 0.022*I_{RhL\alpha}*I_{RhK\alpha} + 0.011*I_{Fe}*I_{RhK\alpha} - 0.055*I_{Pb} \quad (5)$$

In these equations, the asterisk is the FORTRAN symbol for the multiplication operation. The intensities of the lines as measured with the multiple-channel X-ray spectrometer employed with its particular proportional counters and circuitry, are indicated by I. The subscripts indicate the particular elements of the lines for which the intensities were measured.

In determining those equations, 12 samples were used. The 12 samples were then divided and one-half of each was ground. In this case, the samples were prepared by dehydrating samples of slurry and then mixing the residues with boric acid powder to produce briquettes in which the total-solids were 40%, 48%, and 55% forming a total of 72 samples, as indicated in Table IV. Such samples simulate slurries since boric acid powder has X-ray scattering and fluorescent characteristics similar to those of water. The ungroud samples are numbered to 1 to 36 and the corresponding ground samples are numbered 37 to 72. The samples had various approximate proportions of solids, as indicated in the table.

As an indication of the reliability of the method, Table IV represents the actual quantity of copper in the various samples as determined by chemical methods, and the calculated values as determined by the substitution of the measured values of intensity in equation (4). For copper in this particular set of samples, the standard deviation ($\sigma$) of the calculated values, assuming the chemical values were perfectly correct, was 0.0033 with a $rho^2 = 0.998$, where rho is a correlation coefficient.

The data for the corresponding ground and unground samples are presented on the same lines in the table. The deviations in the "actual" amount of copper in each, as measured by chemical methods, sometimes arises partly from the slight inaccuracies in the chemical methods and sometimes in the fact that the grinding process itself alters the chemical composition, and sometimes both. In this table, the symbol 0 represents zero.

in question was being processed for the recovery of copper. Accurate determination of the amount of sulphur was important in this case because it indicated the quantity of one ingredient present that could be responsible for excessive pollution having its origin with the processor. Control of the processing is to be carried out in terms of the sulphur content to minimize pollution while maximizing the recovery of copper.

In an important embodiment of the invention illustrated in FIG. 8, the output signals developed across the charge integrating capacitors are supplied to analog-to-digital converters and digital signals representing the voltages on the capacitors are supplied to a computer that is programmed to solve the parametric equations (e.g., equations (4) and (5)) from which the concentrations of various ingredients or the total-solids or the particle size, can be calculated. Alternatively, cumulative counts from the respective scalers (when they are used) are supplied to the computer. In either event, with this arrangement, the values of the respective concentrations of the respective components and the other terms are applied to a display device DIS, such as a printer, so that the calculated values are displayed. These calculated values, it will be appreciated, are directly proportional to the concentrations of the individual components or the other variables irrespective of interelement effects or variations in the concentration of the total-solids or variations in particle size.

In FIG. 8, there is illustrated, only in a broad way, how a digital signal produced at the output of the computer may be applied to a control point CP of a processor that receives a feed stream FS to control the process in order to produce an output stream which is to be controlled. As illustrated, the control signal is used to

TABLE IV

| STD | ACTUAL | CALCULATED | DEVIATION | STD | ACTUAL | CALCULATED | DEVIATION | |
|---|---|---|---|---|---|---|---|---|
| 1 | .2270000 | .2241637 | −.002836 | 37 | .2280000 | .2240734 | −.003927 | |
| 2 | .1750000 | .1751347 | .000135 | 38 | .1790000 | .1763409 | −.002659 | |
| 3 | .1790000 | .1795536 | .000554 | 39 | .1520000 | .1569948 | .004995 | |
| 4 | .0960000 | .0986339 | .002634 | 40 | .0920000 | .0955231 | .003523 | |
| 5 | .0500000 | .0479138 | −.002086 | 41 | .0580000 | .0582088 | .000209 | |
| 6 | .0400000 | .0401940 | .000194 | 42 | .0420000 | .0406328 | −.001367 | 40% Solids |
| 7 | .0370000 | .0381332 | .001133 | 43 | .0360000 | .0361232 | .000123 | |
| 8 | .1730000 | .1786393 | .005639 | 44 | .1750000 | .1827334 | .007733 | |
| 9 | .1720000 | .1691237 | −.002876 | 45 | .1730000 | .1757350 | .002735 | |
| 10 | .1590000 | .1576760 | −.001324 | 46 | .1600000 | .1609912 | .000991 | |
| 11 | .1850000 | .1777489 | −.007251 | 47 | .1870000 | .1862349 | −.000765 | |
| 12 | .0240000 | .0304269 | .006427 | 48 | .0260000 | .0232047 | −.002795 | |
| 13 | .2270000 | .2298523 | .002852 | 49 | .2280000 | .2276944 | −.000306 | |
| 14 | .1750000 | .1747766 | −.000223 | 50 | .1790000 | .1738948 | −.005105 | |
| 15 | .1790000 | .1787308 | −.000269 | 51 | .1520000 | .1575134 | .005513 | |
| 16 | .0960000 | .0892003 | −.006800 | 52 | .0920000 | .0939358 | .001936 | |
| 17 | .0500000 | .0508120 | .000812 | 53 | .0580000 | .0585081 | .000508 | |
| 18 | .0400000 | .0364562 | −.003544 | 54 | .0420000 | .0414081 | −.000592 | 48% Solids |
| 19 | .0370000 | .0401141 | .003114 | 55 | .0360000 | .0355465 | −.000453 | |
| 20 | .1730000 | .1752514 | .002251 | 56 | .1750000 | .1714175 | −.003583 | |
| 21 | .1720000 | .1680207 | −.003979 | 57 | .1730000 | .1747269 | .001727 | |
| 22 | .1590000 | .1501127 | −.008887 | 58 | .1600000 | .1587249 | −.001275 | |
| 23 | .1850000 | .1825757 | −.002424 | 59 | .1870000 | .1887410 | .001741 | |
| 24 | .0240000 | .0276900 | .003690 | 60 | .0260000 | .0235813 | −.002419 | |
| 25 | .2270000 | .2271436 | .000144 | 61 | .2280000 | .2243282 | −.003672 | |
| 26 | .1750000 | .1740832 | −.000917 | 62 | .1790000 | .1727402 | −.006260 | |
| 27 | .1790000 | .1780174 | −.000983 | 63 | .1590000 | .1569659 | −.002034 | |
| 28 | .0960000 | .1023417 | .006342 | 64 | .0920000 | .0937107 | .001711 | |
| 29 | .0500000 | .0488722 | −.001128 | 65 | .0580000 | .0605993 | .002599 | |
| 30 | .0400000 | .0356516 | −.004348 | 66 | .0420000 | .0423426 | .000343 | 55% Solids |
| 31 | .0370000 | .0363306 | −.000669 | 67 | .0360000 | .0379113 | .001911 | |
| 32 | .1730000 | .1784760 | .005476 | 68 | .1750000 | .1771562 | .002156 | |
| 33 | .1720000 | .1733661 | .001366 | 69 | .1730000 | .1744944 | .001494 | |
| 34 | .1590000 | .1576657 | −.001334 | 70 | .1600000 | .1616568 | .001657 | |
| 35 | .1850000 | .1897159 | .004716 | 71 | .1870000 | .1903264 | .003326 | |
| 36 | .0240000 | .0222503 | −.001750 | 72 | .0260000 | .0224256 | −.003574 | |
| | Unground Samples | | | | Ground Samples | | | |

Similar calculations for sulphur led to a standard deviation of 0.0208 with a $rho^2 = 0.95$.

Accurate determination of copper was important in this particular case because of the fact that the ore body adjust a valve V, as with a servomotor, in response to a deviation in the output of the computer from a norm to urge the deviation to a zero value.

Modifications

The analysis of the composition of a slurry currently sampled may be employed in many ways. The numerical values representing the compositions of different components may be displayed or printed for the convenience of the user. They may also be employed to modify the processing unit in such a way as to regulate the processing. This regulation may be under the control of a single characteristic line or several characteristic lines or ratios of intensity of the analyte to the intensity of another or to the concentration or other measurement. Normally, the regulating signals are determined by computer analysis of the intensity measurements of test samples by means of the equations, such as equations (4) and (5).

It will be understood, of course, that the invention may be practiced in many other ways than those described above, and that the invention is not limited to the particular implementations or examples described. More particularly, it will be understood that where an X-ray tube is employed, the anode may be made of other materials of high atomic number, such as palladium or silver.

While the invention has been described above as applied to a wavelength, or dispersive, spectrometer using a plurality of monochromatizers, it will also be understood that it may be applied to other types of X-ray spectrometers, such as non-dispersive, or energy dispersive, spectrometers. Furthermore, while the invention has been described with particular reference to slurries of a continuously operating processor, it will be understood that it may also be applied to analyses of briquettes, or other solid samples. In some cases, a measurement of the concentration of total-solids is not made, but a measurement is made of the density of the solid sample. For purposes of generalization, it should be borne in mind that concentration of an element is a form of or measure of its partial density.

It will also be understood that discrete pulse counters, or scintillation counters, may sometimes be employed instead of proportional counters. It is sometimes especially desirable to use discrete pulse counters so that it will not be necessary to produce analog voltage signals and then digitize them for direct use by a digital computers. Instead, the outputs of such counters are applied directly to the computer.

Summary

In summary, it is to be emphasized that by measuring the intensities of characteristic lines, other than those which are associated with the components of the mixture undergoing analysis, it is possible to determine the amounts of those ingredients present by making corrections for variations of total-solid content and for variations of particle size, and for interelement effects, from one sample to another. It is also possible to make more accurate measurement of total-solids concentration and of average particle size. Such analyses may be made on-stream and thus give a more rapid indication of changes in functioning of a processing unit and hence facilitate more rapid and more reliable control of the processing unit than has been possible heretofore.

The invention claimed is:

1. In X-ray analytical apparatus for analyzing a sample of material comprising at least one analyte distributed in a matrix containing solids:
   an X-ray source that emits primary X-rays capable of exciting fluorescence in the sample of a first wavelength characteristic of said analyte and that also emits primary X-rays that have second and third wavelengths that are characteristic of the source but not of a component in the sample;
   means for exposing the samples to the aforesaid X-rays where fluorescent X-rays characteristic of said analyte are emitted from the sample in an amount dependent primarily upon the concentration of analyte in the sample and secondarily upon the concentration or density of the matrix in the sample and the average particle size of the matrix and whereby X-rays characteristic of said source are scattered by the sample;
   means for detecting said fluorescent X-rays and said scattered X-rays; and
   means responsive to the detected X-rays for generating different electric signals representative of the intensities of X-rays emitted from the sample at said three wavelengths.

2. In X-ray analytical apparatus as defined in claim 1 wherein said second and third wavelengths are such that the variation of the scattering coefficients of the sample at said second and third wavelengths as a function of the concentration of total-solids in the sample are substantially different from the variation of the scattering coefficients at said two wavelengths as a function of particle size of the sample.

3. In X-ray analytical apparatus as defined in claim 1 wherein the X-rays having said second and third wavelengths are hard and soft respectively.

4. In X-ray analytical apparatus as defined in claim 1 for analyzing a sample in which there are at least two analytes, one of which has an atomic number lower than the other of which has an atomic number greater than the average atomic number of said matrix and in which said X-ray source emits primary X-rays capable of exciting fluorescence in both said analytes and in which the intensity of the flourescence of at least one of the analytes depends in part upon the concentration of the other analyte in the sample because of an interelement effect and in which said detecting means detects X-rays at two wavelengths characteristic of the respective analytes.

5. In X-ray analytical apparatus as defined in claim 1:
   means controlled by said electric signals for generating another electric signal that is proportional to the concentration of said analyte in the sample substantially independently of the concentration or density of the matrix and the particle size of the matrix over substantial ranges of concentration and particle size.

6. In X-ray analytical apparatus as defined in claim 1:
   means controlled by said electric signals for generating another electric signal that is proportional to the concentration of said solids in the sample substantially independent of the particle size of the matrix over substantial ranges of concentration and particle size.

7. In X-ray analytical apparatus as defined in claim 1:
   means controlled by said electric signals for generating another electric signal that is proportional to the concentration or density and particle size of said matrix substantially independent of the particle size of the gangue over substantial ranges of concentration or density and particle size.

8. In X-ray analytical apparatus as defined in claim 4:

means controlled by said electric signals for generating two electric signals that are respectively proportional to the concentrations of said two analytes in the sample substantially independently of the concentration or density of the matrix and the particle size of the matrix over substantial ranges of concentration or density and particle size, and also substantially independently of said interelement effect.

9. In X-ray analytical apparatus for controlling a processor in which a sample is taken on-stream from a slurry;
  means for feeding the on-stream sample to the analytical apparatus of claim 1;
  means for establishing an electric signal representative of a standard value of a characteristic of said slurry; and
  means controlled by said electric signals for automatically adjusting the processor to reduce the deviation of the value of said characteristic from said standard.

10. In X-ray analytical apparatus as defined in claim 1 for analyzing a sample in which there are a plurality of more than two analytes, and in which said X-ray source emits primary X-rays capable of exciting fluorescence characteristic of said analytes and in which the intensity of the fluorescence characteristic of each of two or more of said analytes depends not only upon the concentration of the respective analyte but upon the concentrations of at least one other analyte, due to interelement effects; and
  in which said detecting means detects X-rays emitted from the sample by all said analytes.

11. In X-ray analytical apparatus as defined in claim 10:
  means controlled by said electric signals for generating a plurality of electric signals that are proportional to the concentration of the respective analytes in the sample substantially independently of the concentration or density of the matrix and the particle size of the matrix over substantial ranges thereof and substantially independently of such interelement effects and for generating two electric signals proportional respectively to the concentration or density of the matrix and to the particle size thereof.

12. In X-ray analytical apparatus as defined in claim 10, wherein said detecting means comprises monochromatizers for producing separately detectable beams of X-rays characteristic of said analytes and said source.

13. In an X-ray analytical apparatus as defined in claim 12, wherein such said monochromatizers are in the form of a spectrograph having a dispersion crystal for effecting the monochromatization of the detected rays.

14. In an X-ray analytical apparatus as defined in claim 13, wherein said electric signals are respectively generated by the respective monochromatic beams.

15. In X-ray analytical apparatus as defined in claim 13, wherein the X-rays having said second and third wavelengths are hard and soft respectively.

16. In X-ray analytical apparatus as defined in claim 15, wherein the monochromatizers that detect radiation from said source are tuned to select incoherent scattered radiation in preference to coherent scattered radiation.

17. In X-ray analytical apparatus as defined in claim 10, wherein said X-ray source comprises an X-ray tube having a target composed of a metal of an atomic number that is high compared with the highest atomic number of any of the analytes.

18. In X-ray analytical apparatus as defined in claim 1, wherein said X-ray source comprises a solid mixture that emits characteristic X-rays at discrete wavelengths both in the hard X-ray region and in the soft X-ray region.

19. In a process for analyzing a sample of material comprising at least one analyte distributed in a solid gangue, the steps that comprise:
  selecting a source of X-rays that emits primary X-rays capable of exciting fluorescence in the sample at a first wavelength characteristic of said analyte and that also emits primary X-rays that have second and third wavelengths that are characteristic of a source but not of a component in the sample;
  exposing the sample to the aforesaid X-rays whereby fluorescent X-rays characteristic of said analyte are emitted from the sample in an amount dependent primarily upon the concentration of analyte in the sample and secondarily upon the concentration or density of the matrix in the sample and the average particle size of the matrix whereby X-rays characteristic of said source are scattered by the sample;
  detecting said fluorescent X-rays and said scattered X-rays; and
  utilizing said detected X-rays to generate different electric signals representative of the intensities of X-rays detected at said three wavelengths.

20. In a process as defined in claim 19, wherein a source is selected for which said second and third wavelengths are such that the variation of the scattering coefficients of the sample at said second and third wavelengths as a function of the concentration or density of solids in the sample are substantially different from the variation of the scattering coefficients at said two wavelengths as a function of particle size of the sample.

21. In a process as defined in claim 19, wherein a solid radioactive source is selected having such two characteristic lines.

22. In a method for determining the concentration of an element in a matrix consisting of a mixture of compounds of other elements by measuring the intensities of secondary X-rays of different wavelengths emitted from said element in response to exposure of said mixture to primary X-rays, the steps of:
  exposing said mixture to a heterochromatic beam of primary X-rays including wavelengths capable of exciting X-ray re-emissions from said mixture at at least the following wavelengths:
    (a) a wavelength characteristic of said element;
    (b) a soft wavelength different from any wavelength characteristic of said element; and
    (c) a hard wavelength different from any wavelength cahracteristic of said element;
  measuring the intensities of the respective X-ray emissions at each of said three wavelengths; and
  correcting the apparent concentration of said element indicated by the intensity of said re-emission at wavelength (a) for the influence thereupon of said matrix, as determined by the intensities of said X-ray re-emissions at both wavelength (b) and wavelength (c).

* * * * *